United States Patent [19]

Tsipouras et al.

[11] Patent Number: 5,089,530
[45] Date of Patent: Feb. 18, 1992

[54] NOVEL FERMENTATION PRODUCT WITH ANTIPARASITIC ACTIVITY

[75] Inventors: Athanasios Tsipouras, Rahway; Dan A. Ostlind, Watchung; Otto D. Hensens, Red Bank; Deborah L. Zink, Manalapan, all of N.J.

[73] Assignee: Merck & Co., Inc., Rahway, N.J.

[21] Appl. No.: 562,353

[22] Filed: Aug. 3, 1990

[51] Int. Cl.$^5$ .............................................. A61K 31/12
[52] U.S. Cl. ..................................... 514/682; 568/328
[58] Field of Search ........................ 568/328; 514/682

[56] References Cited

U.S. PATENT DOCUMENTS

| | | | |
|---|---|---|---|
| 4,414,226 | 11/1983 | Ikushima et al. | 514/468 |
| 4,530,845 | 7/1985 | Ikushima et al. | 514/453 |
| 4,639,467 | 1/1987 | Celino | 514/468 |
| 4,837,399 | 6/1989 | Baker et al. | 514/468 |
| 4,839,382 | 6/1989 | Maestrone et al. | 514/453 |
| 4,927,848 | 5/1990 | Konishi et al. | 514/453 |

FOREIGN PATENT DOCUMENTS 004128 of 0000 European Pat. Off. ............ 514/453

OTHER PUBLICATIONS

Byrne et al., Chem. Abst., vol. 108, #128,435m, (1988).
Kawai, K. et al., (1982), *Res. Comm. Chem. Path. Pharm.*, 36, pp. 429–438.
Peterson, R. E. and Grove, M. D., (1983), *Appl. Environ. Microbiol.*, 45, pp. 1937–1938.
Stack, M. E. et al., (1977), *Appl. Environ. Microbiol.*, 33, pp. 351–355.
Wirth, J. C. et al., (1964), *Phytochemistry*, 4, pp. 505–509.
Just, G., and Day, W. C., (1963), *Can. J. Chem.*, 41, pp. 74–79.
Ito, Y. et al., (1973), *J. Biochem.*, 74, pp. 805–810.

Primary Examiner—James H. Reamer
Attorney, Agent, or Firm—Hesna J. Pfeiffer; William H. Nicholson

[57] ABSTRACT

The fermentation of a fungal organism identified as *Chrysosporium meridarium* produces a novel binaphthalene compound which is a highly potent antiparasitic, insecticidal, and anthelminthic agent.

4 Claims, 1 Drawing Sheet

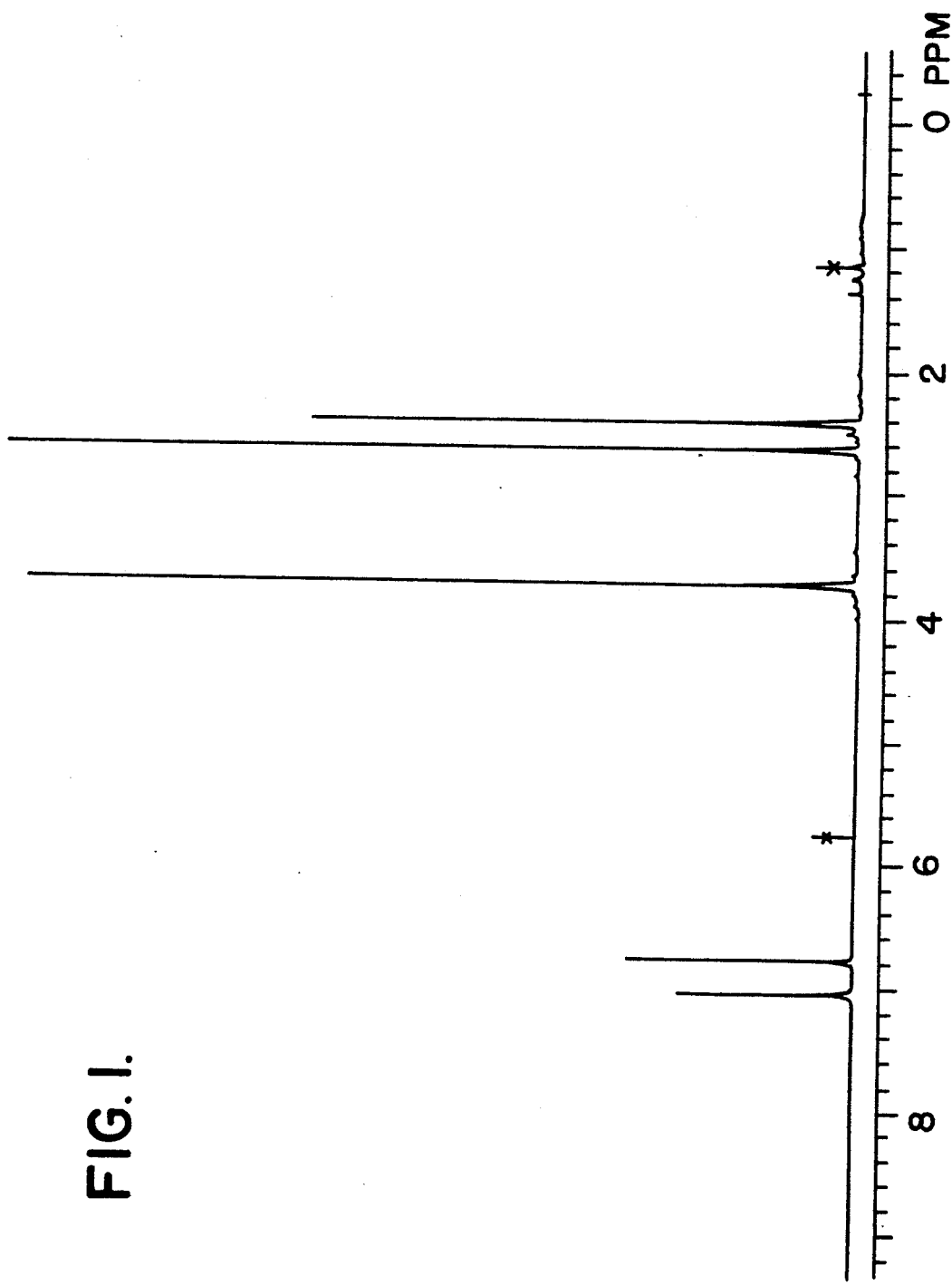
FIG. I.

NOVEL FERMENTATION PRODUCT WITH ANTIPARASITIC ACTIVITY

BACKGROUND OF THE INVENTION

The present invention describes the production of a novel binaphthalene compound produced during the fermentation of a fungal organism identified as *Chrysosporium meridarium*. The novel compound resembles xanthomegnin, however, the novel compound possesses significant structural features which readily differentiate it from any known prior art compounds.

According to the present invention, the novel compound has been discovered to have potent antiparasitic, insecticidal, and anthelminthic activity against organisms which effect human and animal health.

OBJECTS OF THE INVENTION

It is an object of the present invention to provide a novel compound, and a method of preparing such compound, from microbiological products. It is a further object of the present invention to provide a method for the recovery and purification of the novel compound from microbial fermentation broth. It is an additional object of the present invention to provide a method of treatment of a parasitic or insect infestation, in particular a method employing an anthelminthic, acaracidal or trematocidal agent. It is therefore another object of the present invention to provide novel antiparasitic and insecticidal compositions containing the novel compound. These and other objects of the present invention will be apparent from the following description.

SUMMARY OF THE INVENTION

This invention is concerned with a novel chemical compound. In particular it is concerned with a novel binaphthalene compound which is produced by the fermentation of a nutrient medium by a species of fungal microorganism identified as *Chrysosporium meridarium*. This novel compound was discovered to have antiparasitic and insecticidal activity, in particular anthelminthic, acaracidal, and trematocidal activity. Compositions containing the novel compound of the present invention, for antiparasitic and insecticidal use are disclosed.

BRIEF DESCRIPTION OF THE DRAWING

FIG. 1—The $^1$H-NMR spectrum of the novel compound of the present invention, is shown as measured at 300 MHz using a Varian XL-300 NMR spectrometer.

DETAILED DESCRIPTION OF THE INVENTION

The novel compound of the present invention (hereinafter referred to as Compound I) is 1,1',8,8' tetrahydroxy-3,3'-dimethoxy-6,6'-dimethyl-7,7'-diacetyl-2,2'-binaphthalene, molecular weight 490, with chemical structure of Formula I:

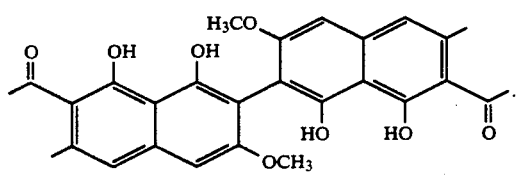

I

The structure of Compound I has been determined by X-ray crystallography and detailed analysis of the various spectral characteristics of the compound, in particular its nuclear magnetic resonance, mass, ultraviolet and infrared spectra.

FIG. 1 shows the nuclear magnetic resonance (NMR) spectrum of Compound I. The $^1$H-NMR spectrum was recorded at 300 MHz (DMSO-d6) on a Varian XL300 NMR spectrometer. Chemical shifts are shown in ppm relative to tetramethylsilane at zero ppm using the solvent peak at 2.49 ppm as the internal standard.

The novel process for preparing Compound I comprises fermentation of a nutrient medium with *Chrysosporium meridarium* or mutants thereof. This organism is designated MF-5343 in the culture collection of Merck and Co., Inc., Rahway, N.J. A sample of this culture, capable of producing the compound of the present invention has been deposited, without restriction as to availability, in the permanent culture collection of the American Type Culture Collection at 12301 Parklawn Drive, Rockville, Md., 20852, and has been assigned the accession number ATCC 74009.

Colonies of *Chrysosporium meridarium* ATCC 74009 attained 20 to 27 mm in diameter following 10 days of growth on potato-dextrose agar (Difco) at 25° C. The colonies were slightly raised, about 1-2 mm deep, with a felty surface. Colonies had some erect hyphal strands, and were sometimes slightly granular, radially ridged or rivulose, with appressed to submerged, minutely fringed margins. The colony surface was at first dry and white to pale yellow, but soon became bright yellow with a relatively wide, white margin. Colony color was Naphthalene Yellow, Barium Yellow, Mustard Yellow, Wax Yellow, Strontian Yellow, with color designations from Ridgway, R., Color Standards and Nomenclature, Washington, D.C., 1912. The colonies when viewed in reverse were plicate-folded, hyaline at the margin, and became yellow inward, and yellow-brown to brown at the center, color designations Cartridge Buff, Colonial Buff, Honey Yellow, Clay Color, Verona Brown, and Dresden Brown, from Ridgway, R., Color Standards and Nomenclature, Washington D.C., 1912. Odors and exudates were absent.

Conidiophores were micronematous to semi-macronematous, integrated, variable in length, generally less than 50 μm long, irregularly branched or not branched, with branches usually at acute angles. Conidiogenesis was arthosporic, terminal and intercalary. Conidia were 4.5-6 μm × 3-5 μm, broadly elliptical, pyriform or subglobose, with one or two truncate basal scars, smooth to faintly verruculose, hyaline to pale grayish yellow in 3% KOH. Hyphae were septate, branched, undulating to tortuous, and 0.5 to 4 μm in diameter.

The above description correlates with the description of *Chrysosporium meridarium* in Carmichael, J. W., (1962), Chrysosporium and Some Other Aleurosporic Hyphomycetes, *Can. J. Botany*, 40, pp. 1137-1173.

The above description is illustrative of *Chrysosporium meridarium*, ATCC 74009, which can be employed in the present invention. The present invention also embraces mutants of the above described microorganism. For example, those mutants which are obtained by natural selection recombinant techniques such as protoplast fusion, gene transfer and the like, or those produced by mutating agents, including ionizing radiation, such as ultraviolet irradiation, or chemical mutagens such as nitrosoguanidine or the like treatments are also included.

Compound I is produced during the aerobic fermentation of suitable aqueous nutrient media under conditions described hereinafter, with a producing strain of *Chrysosporium meridarium*, ATCC 74009. Aqueous media such as those used for the production of many anthelminthic substances are suitable for use in this process for the production of the binaphthelenic compound of the present invention. Such nutrient media contain sources of carbon and nitrogen assimilable by the microorganism, and generally low levels of inorganic salts. In addition, the fermentation media may contain traces of metals necessary for the growth of the microorganism, and production of the desired compound. These are usually present in sufficient concentrations in the complex sources of carbon and nitrogen which may be used as nutrient sources but can, of course, be added separately to the medium if desired.

In general, carbohydrates such as, dextrose, sucrose, maltose, lactose, dextran, cerelose, corn meal, oat flour, and the like, and starches are suitable sources of assimilable carbon in the nutrient media. The exact quantity of the carbon source which is utilized in the medium will depend, in part, upon the other ingredients in the medium but it is usually found that an amount of carbohydrate between 5.5 and 15% by weight of the medium is satisfactory. These carbon sources can be used individually or several such carbon sources may be combined in the same medium.

Various nitrogen sources such as yeast hydrolysates, yeast autolysates, yeast cells, tomato paste, corn meal, oat flour, soybean meal, casein hydrolysates, yeast extracts, corn steep liquors, distillers solubles, cottonseed meal, meat extract and the like, are readily assimilable by *Chrysosporium meridarium*, ATCC 74009, in the production of Compound I. The various sources of nitrogen can be used alone or in combination in amounts ranging from 0.2 to 6% by weight of the medium.

Among the nutrient inorganic salts, which can be incorporated in the culture medium are the customary salts capable of yielding sodium, potassium, magnesium, ammonium, calcium, phosphate, sulfate, chloride, carbonate, and like ions. Also included are trace metals such as cobalts, manganese, and the like.

It should be noted that the media described hereinbelow and in the Examples, are merely illustrative of the wide variety of media which may be employed, and are not intended to be limitative.

The fermentation employing *Chrysosporium meridarium*, ATCC 74009, can be conducted at temperatures ranging from about 20° C. to about 28° C. For optimum results, it is most convenient to conduct these fermentations at a temperature in the range from about 22° C. to about 25° C. Temperatures of about 22° to 23° C. are most preferred. The pH of the nutrient medium suitable for producing the instant compounds can vary from about 5.0 to 8.5 with a preferred pH range from about 6.0 to 7.5.

Small scale fermentations are conveniently carried out by placing suitable quantities of nutrient medium in a flask employing known sterile techniques, inoculating the flask with either spores or vegetative cellular growth of *Chrysosporium meridarium*, ATCC 74009, loosely stoppering the flask with cotton and permitting the fermentation to proceed at a temperature of about 23° C. on a rotary shaker at about 95 to 300 rpm for about 2 to 21 days. For larger scale work, it is preferable to conduct the fermentation in suitable tanks provided with an agitator and a means of aerating the fermentation medium. The nutrient medium is made up in the tank and after sterilization is inoculated with a source of vegetative growth of *Chrysosporium meridarium*, ATCC 74009. The fermentation is allowed to continue for 1 to 8 days while aerating the nutrient medium at a temperature in the range of about 22° to 23° C., without agitation.

The novel compound of this invention is found primarily in the mycelium on termination of the *Chrysosporium meridarium*, ATCC 74009 fermentation and may be removed and separated therefrom as described below.

The separation of the novel compound from the whole fermentation broth and the recovery of said compound is carried out by solvent extraction and application of chromatographic fractionations with various chromatographic techniques and solvent systems.

Compound I has slight solubility in water, but is soluble in organic solvents. This property may be conveniently employed to recover the compound from the fermentation broth. Thus, in one recovery method, the whole fermentation broth is combined with approximately an equal volume of an organic solvent. While any organic solvent may be employed, it is preferable to use a water immiscible solvent such as ethyl acetate, methylene chloride, chloroform, methyl ethyl ketone and the like. Generally several extractions are desirable to achieve maximum recovery. The solvent removes Compound I as well as other substances lacking the antiparasitic activity of the instant compound. If the solvent is a water immiscible one, the layers are separated and the organic solvent is evaporated under reduced pressure. If the solvent is water miscible, it can be extracted with a water immiscible solvent to separate the entrained water. This solvent can then be concentrated under reduced pressure. The residue is placed onto a chromatography column containing preferably, silica gel. The column retains the desired products and some impurities, but allows many of the impurities, particularly the nonpolar impurities, to pass through. The column is washed with a moderately polar organic solvent such as methylene chloride or chloroform, to further remove impurities, and is then washed with a mixture of methylene chloride or chloroform and an organic solvent of which acetone, ethyl acetate, methanol, ethanol and the like are preferred. The solvent is evaporated and the residue further chromatographed using column chromatography, thin layer chromatography, preparative layer chromatography, high pressure liquid chromatography and the like, with silica gel, aluminum oxide, dextran gels and the like, as the chromatographic medium, with various solvents and combinations of solvents as the eluent. Thin layer, high pressure, liquid and preparative layer chromatography may be employed to detect the presence of, and to isolate the instant compound.

Compound I isolated as described above was a yellow powder and gave a single peak by HPLC (4.6×250 mm Zorbax C18 column, equilibrated with 80% methanol in water and run at 1 mL/minute, at 40° C.) at 14.1 minutes. U.V. maxima appeared at 235, 260, and 381 nm in acetonitrile, and at 211, 246, 272, and 389 nm in aqueous sodium hydroxide. I.R. peaks (melt) appeared at 3310, 2930, 1737, 1685, 1607, 1543, 1521, 1457, 1429, 1283, 1200, 1167, 1125, 1033, 983, and 826 cm$^{-1}$. HRMS indicated a formula of $C_{28}H_{26}O_8$ (calculated m/z 490.1628, m/z found 490.1609). NMR ($^{13}$C, d6-DMSO) showed peaks at 21.7, 32.1, 55.5, 97.4, 107.3, 108.6, 118.1, 119.1, 133.9, 137.4, 154.7, 158.9, 159.5, and 204.2 ppm.

The use of the foregoing techniques as well as others known to those skilled in the art, will afford purified compositions containing Compound I. The presence of Compound I is determined by analyzing the various chromatographic fractions for biological activity against selected parasites, or physicochemical characteristics.

According to the present invention, it has been discovered that Compound I is an effective antiparasitic agent useful for the control of parasites infecting humans, livestock and other animals as well as poultry and other birds. Compound I has significant parasiticidal activity as an anthelminthic, insecticide and acaricide, in human and animal health, and in agriculture.

The disease or group of diseases described generally as helminthiasis is due to infection of an animal host with parasitic worms known as helminths. Helminthiasis is common in humans and is a prevalent, serious economic problem in domesticated animals such as swine, sheep, horses, cattle, goats, dogs, cats and poultry. Among the helminths, the group of worms described as trematodes causes widespread and often times serious infection in various species of animals including humans. The most common genera of trematodes infecting the animals referred to above are Fasciola, Fasciolopsis, Heterophyes, Metagonimus, Paragonimus, Clonorchis, Episthorchis, Troglotrema, and Schistosoma.

The parasitic infections known as helminthiasis lead to anemia, malnutrition, weakness, weight loss, severe damage to the walls of the intestinal tract and other tissues and organs and, if left untreated, may result in death of the infected host. Compound I has unexpectedly high activity against these parasites, and in addition is active against arthropod ectoparasites of animals and birds, such as ticks, mites, lice, fleas, biting insects and such migrating dipterous larvae as Hypoderma sp. in cattle, Gastrophilus in horses, and Cuterebra sp. in rodents.

Compound I is also useful against parasites which infect humans. In addition to the trematodes, other common genera of parasites of the gastro-intestinal tract of man are nematodes such as Ancylostoma, Necator, Ascaris, Strongyloides, Trichinella, Capillaria, Trichuris, and Enterobius, and cestodes (tapeworms) such as Diphyllobothrium, Taenia, Hymenolepis, and Echinococcus. Other medically important genera of nematode parasites which are found in the blood or other tissues and organs outside of the gastro-intestinal tract are the filiarial worms such as Wuchereria, Brugia, Onchocerca, Laoa, Dipetalonema, Mansonella, and Dracunculus and extra-intestinal stages of the intestinal worms Strongyloides and Trichinella. Compound I is also of value against arthropods parasitizing man, as well as biting insects and other dipterous pests causing annoyance to man.

Compound I is also active against household pests such as the cockroach (Blatella sp.), clothes moth (Tineola sp.), carpet beetle (Attagenus sp.), and the housefly *Musca domestica*.

Compound I is also useful against insect pests of stored grains such as Tribolium sp., Tenebrio sp. and of agricultural plants such as spider mites, (Tetranychus sp.), aphids (Acyrthiosiphon), migratory orthopterans such as locusts, and immature stages of insects living on plant tissue. Compound I is useful as a nematocide for the control of soil nematodes and plant parasites such as Meloidogyne sp., which may be of importance to agriculture.

Compound I may be administered orally in a unit dosage form such as a capsule, bolus or tablet, or as a liquid drench where used as an anthelminthic in mammals. The drench is normally a solution, suspension or dispersion of Compound I usually in water together with a suspending agent such as bentonite and a wetting agent or like excipient. Generally, the drenches also contain an antifoaming agent. Drench formulations generally contain from about 0.001 to 0.5% by weight of Compound I. Preferred drench formulations may contain from 0.01 to 0.1% of Compound I by weight. The capsules and boluses comprise Compound I admixed with a carrier vehicle such as starch, talc, magnesium stearate, or dicalcium phosphate.

Where it is desired to administer Compound I orally in a dry, solid unit dosage form, capsules, boluses or tablets containing the desired amount of Compound I usually are employed. These dosage forms are prepared by intimately and uniformly mixing Compound I with suitable finely divided diluents, filler, disintegrating agents and/or binders such as starch, lactose, talc, magnesium stearate, vegetable gums and the like. Such unit dosage formulations may be varied widely with respect to their total weight and content of Compound I depending upon factors such as the type of host animal to be treated, the severity and type of infection and the weight of the host.

When Compound I is to be administered via an animal feedstuff, it is intimately dispersed in the feed or used as a top dressing or in the form of pellets which may then be added to the finished feed or optionally fed separately.

Alternatively, Compound I may be administered to animals parenterally, for example, by intraruminal, intramuscular, intratracheal, or subcutaneous injection in which event Compound I is dissolved or dispersed in a liquid carrier vehicle. For parenteral administration, Compound I is suitably admixed with an acceptable vehicle, preferably of the vegetable oil variety such as peanut oil, cotton seed oil and the like. Other parenteral vehicles such as organic preparations using solketal, glycerol, formal and aqueous parenteral formulations are also used. Compound I is dissolved or suspended in the parenteral formulations generally containing from 0.005 to 5% by weight of Compound I.

Although Compound I has its primary use in the treatment and/or prevention of helminthiasis, it is also useful in the prevention and treatment of diseases caused by other parasites, for example, arthropod parasites such as ticks, lice, fleas, mites and other biting insects in domesticated animals and poultry. It is also effective in treatment of parasitic diseases that occur in other animals including humans. The optimum amount to be employed for best results will, of course, depend upon the species of animal to be treated and the type and severity of parasitic infection or infestation. Generally, good results are obtained with Compound I by the oral administration of about 0.001 to 100 mg per kg of animal or human body weight, with 0.1 to 100 mg/kg preferred, such total dose being given at one time or in divided doses over a relatively short period of time, such as 1-5 days. Excellent control of such parasites is obtained in animals by administering Compound I from about 0.1 to 100 mg per kg of body weight in a single dose. Repeat treatments are given as required to combat re-infections and are dependent upon the species of parasite and the husbandry techniques being employed. The techniques for administering these materials to animals are known to those skilled in the veterinary field.

When Compound I is administered as a component of the feed of the animals, or dissolved or suspended in the drinking water, compositions are provided in which Compound I is intimately dispersed in an inert carrier or diluent. By inert carrier is meant one that will not react with Compound I and one that may be administered safely to animals. Preferably, a carrier for feed administration is one that is, or may be, an ingredient of the animal ration.

Suitable compositions include feed premixes or supplements in which Compound I is present in relatively large amounts and which are suitable for direct feeding to the animal or for addition to the feed either directly or after an intermediate dilution or blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like. Compound I is intimately dispersed throughout the carrier by methods such as grinding, stirring, milling or tumbling. Compositions containing from about 0.005 to 2.0% by weight of Compound I are particularly suitable as feed premixes. Feed supplements, which are fed directly to the animal, contain from about 0.0002 to 0.3% by weight of Compound I.

Such supplements are added to the animal feed in an amount to give the finished feed the concentration of Compound I desired for the treatment and control of parasitic diseases. Although the desired concentration of Compound I will vary depending upon the factors previously mentioned, Compound I is usually fed at concentrations of between 0.0001 to 0.02% in the feed in order to achieve the desired anti-parasitic result.

Compound I has a broad spectrum of activity against many internal parasites at low dosage levels and in many different animals. At levels of about 5 mg per kg of animal body weight, concentrated mixtures of Compound I are fully active in sheep against *Haemonchus contortus*. In rodents, such as mice, parasites such as *Fasciola hepatica* and *Dipetalogaster maximus* were successfully treated by the oral administration of Compound I, or of the concentrates obtained from the extraction of the fungal mycelia containing Compound I.

Compound I is also useful in combatting agricultural pests that inflict damage upon crops while they are growing or while in storage. The compound is applied using known techniques as sprays, dusts, emulsions and the like, to the growing or stored crops to effect protection from such agricultural pests.

Compound I is especially useful in animals against ectoparasites as demonstrated by its effectiveness against *Dipetalogaster maximus* and has the additional advantage of being useful against endoparasitic helminths such as *Fasciola hepatica* which can infect humans and animals.

Compound I may be administered orally, topically, or parenterally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

The pharmaceutical compositions containing Compound I may be in a form suitable for oral use, for example, as tablets, troches, lozenges, aqueous or oily suspensions, dispersible powders or granules, emulsions, hard or soft capsules, or syrups or elixirs. Compositions containing Compound I intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparation. Tablets containing Compound I in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, or alginic acid; (3) binding agents such as starch, gelatin or acacia, and (4) lubricating agents such as magnesium stearate, stearic acid or talc. The tablets may be uncoated or they may be coated by known techniques to delay intestinal tract absorption and thereby provide a sustained action over a longer period. For example, a time delay material such as glyceryl monostearate or glyceryl distearate may be employed. They may also be coated by the techniques described in the U.S. Pat. Nos. 4,256,108; 4,160,452; and 4,265,874 to form osmotic therapeutic tablets for controlled release.

In some cases, formulations containing Compound I for oral use may be in the form of hard gelatin capsules wherein Compound I is mixed with an inert solid diluent, for example, calcium carbonate, calcium phosphate or kaolin. They may also be in the form of soft gelatin capsules wherein Compound I is mixed with water or an oil medium, for example peanut oil, liquid paraffin, or olive oil.

Aqueous suspensions normally contain Compound I in admixture with excipients suitable for the manufacture of aqueous suspensions. Such excipients may be:
(1) suspending agents such as sodium carboxymethylcellulose, methylcellulose, hydroxypropylmethylcellulose, sodium alginate, polyvinyl-pyrrolidone, gum tragacanth and gum acacia;
(2) dispersing or wetting agents which may be:
 (a) a naturally-occuring phosphatide such as lecithin,
 (b) a condensation product of an alkylene oxide with a fatty acid, for an example, polyoxyethylenestearate,
 (c) a condensation product of ethylene oxide with a long chain aliphatic alcohol, for example, heptadeca-ethyleneoxycetanol,
 (d) a condensation product of ethylene oxide with a partial ester derived from a fatty acid and hexitol such as polyoxyethylene sorbitol monooleate, or
 (e) a condensation product of ethylene oxide with a partial ester derived from a fatty acid and a hexitol anhydride, for example polyoxyethylene sorbitan monooleate.

These aqueous suspensions may also contain one or more preservatives, for example, ethyl or n-propyl p-hydroxybenzoate; one or more coloring agents; one or more flavoring agents; and one or more sweetening agents such as sucrose or saccharin.

Oily suspensions may be formulated by suspending Compound I in a vegetable oil, for example arachis oil, olive oil or coconut oil, or in a mineral oil such as liquid paraffin. The oily suspensions may contain a thickening agent, for example beeswax, hard paraffin or cetyl alcohol. Sweetening agents and flavoring agents may be added to provide a palatable oral preparation. These compositions may be preserved by the addition of an antioxidant such as ascorbic acid.

Dispersible powders and granules are suitable for the preparation of an aqueous suspension containing Compound I. They provide Compound I in admixture with a dispersing or wetting agent, a suspending agent and one or more preservatives. Suitable dispersing or wetting agents and suspending agents are exemplified by those already mentioned above. Additional excipients, for example, those sweetening, flavoring and coloring agents described above may also be present.

The pharmaceutical compositions of the present invention containing Compound I may also be in the form of oil-in-water emulsions. The oily phase may be a vegetable oil such as olive oil or arachis oils, or a mineral oil such as liquid paraffin or a mixture thereof. Suitable emulsifying agents may be (1) naturally-occurring gums such as gum acacia and gum tragacanth, (2) naturally-occuring phosphatides such as soy bean and lecithin, (3) esters or partial esters derived from fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Syrups and elixirs may be formulated with sweetening agents, for example, glycerol, propylene glycol, sorbitol or sucrose. Such formulations may also contain a demulcent, a preservative and flavoring and coloring agents.

The pharmaceutical compositions containing Compound I may be in the form of a sterile injectable aqueous or oleagenous suspension. This suspension may be formulated according to known methods using those suitable dispersing or wetting agents and suspending agents which have been mentioned above. The sterile injectable preparation may also be a sterile injectable solution or suspension of Compound I in a non-toxic parenterally-acceptable diluent or solvent, for example as a solution in 1,3-butanediol. Among the acceptable vehicles and solvents that may be employed are water. Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compound I may also be administered in the form of suppositories for rectal administration. These compositions can be prepared by mixing Compound I with a suitable non-irritating excipient which is solid at ordinary temperatures but liquid at the rectal temperature and will therefore melt in the rectum to release Compound I. Such materials are cocoa butter and polyethylene glycols.

For topical use, creams, ointments, jellies, solutions or suspensions, etc., containing Compound I are employed.

The amount of Compound I that may be combined with the carrier materials to produce a single dosage form will vary depending upon the host treated and the particular mode of administration. For example, a formulation intended for the oral administration of humans may contain 0.001 mg to 100 mg of Compound I with an appropriate and convenient amount of carrier material which may vary from about 5 to about 95 percent of the total composition. Dosage unit forms will generally contain from about 0.001 mg to about 100 mg of Compound I.

It will be understood, however, that the specific dose level for any particular patient will depend upon a variety of factors including the age, body weight, general health, sex, diet, time of administration, route of administration, drug combination and the severity of the particular disease undergoing therapy.

The following examples are being provided in order that the present invention may be more fully understood. The following examples illustrate the invention but are not to be construed as limiting.

EXAMPLE 1

| Component | Amount per Liter |
|---|---|
| A: MEDIUM I pH 6.8 | |
| Corn Steep Liquor | 5.0 g |
| Tomato Paste | 40.0 g |
| Oat Flour | 10.0 g |
| Glucose | 10.0 g |
| $FeSO_4.H_2O$ | 10.0 mg |
| $MnSO_4.H_2O$ | 10.0 mg |
| $CuCl_2.H_2O$ | 0.25 mg |
| $CaCl_2$ | 1.0 mg |
| $H_3BO_3$ | 0.56 mg |
| $(NH_4)_2Mo_7O_{24}.4H_2O$ | 0.19 mg |
| $ZnSO_4.7H_2O$ | 2.0 mg |
| B: MEDIUM II | |
| Dextrose | 150.0 g |
| Urea | 4.0 g |
| NZ-Amine A | 4.0 g |
| $K_2HPO_4$ | 0.5 g |
| $MgSO_4.7H_2O$ | 0.25 g |
| KCl | 0.25 g |
| $ZnSO_4.7H_2O$ | 0.9 g |
| $CaCO_3$ | 16.5 g |

Lyophiles of seed cultures were prepared by seeding 54 mL of Medium I with *Chrysosporium meridarium* ATCC 74009 in a 250 mL baffled Erlenmeyer flask, and incubating at 28° C., 220 rpm for 3 days. The resulting culture biomass was macerated to a smooth suspension, and 2.5 mL volumes were added to 0.5 mL of 60% glycerol (volume/volume). Aliquots of this glycerol mixture were frozen and stored at −80° C. and used to prepare seed cultures.

A lyophile of ATCC 74009 was aseptically transferred to a 250 mL plain Erlenmeyer flask containing 54 mL of Medium I. The flask was shaken at 220 rpm, 25° C., on a rotary shaker with a 2 inch throw, for 2 days. About 12 mL of this culture was transferred to each of 6 2L Erlenmeyer flasks containing 250 mL of Medium II and 70 g of vermiculite. The culture was mixed vigorously and incubated at 22° to 23° C. for 21 days without agitation.

EXAMPLE 2

Medium Preparation

Medium I was prepared with the ingredients listed under Medium I, Example 1, using distilled water. The pH was adjusted to 6.8 prior to sterilization. Medium I was dispensed at 54 mL per 250 mL plain Erlenmeyer flask. Each flask was plugged with cotton and sterilized by autoclaving for 20 minutes at 121° C., 15 psi. Following sterilization the flasks were removed from the autoclave and cooled to room temperature.

Medium II was prepared with the ingredients listed under Medium II, Example 1, using distilled water. The pH of the medium was not adjusted. The medium was dispensed at 250 mL per 500 mL plain Erlenmeyer flask. Each flask was plugged with cotton and sterilized by autoclaving for 15 minutes at 121° C., 15 psi. Following sterilization the flasks were removed from the autoclave and cooled to room temperature.

70 grams of vermiculite was placed into each of six 2L plain Erlenmeyer flasks. The flasks were plugged with cotton and sterilized by autoclaving for 60 minutes at 121° C., 15 psi. Following sterilization the flasks were removed from the autoclave and cooled to room temperature.

Culture Development

A lyophilized tube of ATCC 74009 was aseptically opened and the contents was used to inoculate a flask of Medium I. The flask was placed on a gyrotory shaker with a 2 inch throw at 220 rpm, 25° C. for 2 days to produce a "seed" culture.

Following incubation, 12 mL of the seed culture was used to aseptically inoculate a flask of Medium II. The seed inoculum in Medium II was mixed, and the entire contents of the flask was aseptically transferred to the 2L flask containing vermiculite, and mixed vigorously. These "production" cultures were incubated without agitation for 21 days at 22° to 23° C.

EXAMPLE 3

Compound Isolation

Six "production" culture flasks were prepared as in Example 2. The cultures were extracted using the organic solvent methyl ethyl ketone. Into each 2L production culture flask was transferred 250 mL of methyl ethyl ketone. The flasks of mixture were shaken for 30 minutes at 160 rpm in a tengential shaker at 23° C. The extract was filtered through a sintered glass funnel with an overlayer of diatomaceous earth. The organic layer was evaporated to dryness under vacuum.

The dried extract was then dissolved in methylene chloride and chromatographed on a 1 liter column (2 inch diameter) containing 6 inches of silica-gel in methylene chloride. Chromatography was done using E. Merck silica-gel 60, 0.04 to 0.06 mm particle size, and equilibrated with methylene chloride, using 7 psi of nitrogen pressure, at a flow rate of 60 mL per minute. After applying the extract to the silica-gel column, the column was washed with several column volumes of methylene chloride and was developed with a gradient of methanol (0–100% in methylene chloride). Column fractions were collected and tested for biological activity. Biological activity was found in the yellow colored fractions which were pooled, dried and rechromatographed on silica-gel as described above, except that 1% methanol in methylene chloride was used. Fractions containing the yellow colored compound were pooled. This product was determined to be Compound I and was judged to be greater than 95% pure by thin layer chromatography and high pressure liquid chromatography.

EXAMPLE 4

Standard laboratory mouse chow was supplemented with Compound I at various concentrations (0.0288%, 0.0468% and 0.1%, by weight). The Compound I supplemented chow was fed to Charles River CD-1 mice, ad libitum, for five days. The total dose of Compound I was between 0.1 and 100 mg/kg/mouse.

On the fifth day, *Dipetalogaster maximus* insects (Hemiptera), at the first-instar stage of metamorphosis, were fed a blood meal on mice fed either chow supplemented with Compound I, or unsupplemented chow. The insects were then kept at 80° F. and 50% humidity, for observation every 24 hours. The insects were observed for viability, motility (paralysis), morphology, and metamorphological progression (molting).

The results of this experiment are shown in Table I. The results demonstrate the effective antiparasitic activity of Compound I against the ectoparasite *Dipetalogaster maximus*.

TABLE I

| % compound in chow | Number of mice | Number of D. maximus fed | Condition of insects |
| --- | --- | --- | --- |
| 0 | 1 | 3 | normally molted. |
| 0 | 1 | 2 | normally molted. |
| 0.0288 | 1 | 2 | one dead; and one paralyzed. |
| 0.0468 | 1 | 3 | one dead; and two paralyzed. |
| 0.1 | 1 | 2 | two dead. |

EXAMPLE 5

Charles River CD-1 mice were fed standard laboratory mouse chow, ad libitum, for six days, which was supplemented with either Compound I at 0.1% or 0.15%, or the known anthelminthic agent rafoxanide at 0.0125%, or unsupplemented standard laboratory mouse chow. All mice were known to harbor the liver fluke *Fasciola hepatica*. The total dose of Compound I was between 0.1 and 100 mg/kg/mouse.

After the sixth day of treatment, the mice were sacrificed, and their livers were removed and crushed between two glass plates. The crushed livers were examined to determine the physical condition of the liver flukes.

The results are shown in Table II. The results show the effective antiparasitic activity of Compound I against the endoparasite *Fasciola hepatica*, as demonstrated by the absence, or abnormal appearance, of the flukes and a reduction of fluke-related liver scar tissue.

TABLE II

| Treatment | % Dietary level | Number of flukes | Morphological condition of flukes | Condition of liver[1] |
| --- | --- | --- | --- | --- |
| None | 0 | 2 | normal | heavily scarred |
| None | 0 | 1 | normal | heavily scarred |
| None | 0 | 2 | normal | heavily scarred |
| Compound I | 0.15 | 0 | — | moderately scarred |
| Compound I | 0.1 | 2 | abnormal | moderately scarred |

TABLE II-continued

| Treatment | % Dietary level | Number of flukes | Morphological condition of flukes | Condition of liver[1] |
|---|---|---|---|---|
| Compound I | 0.1 | 0 | — | lightly scarred |
| Compound I | 0.1 | 0 | — | lightly scarred |
| Rafoxanide | 0.0125 | 1 | abnormal | moderately scarred |

[1]Scarring of the liver results from parenchymal damage caused by migrating liver flukes. Heavy scarring-21% to 30% of liver; moderate scarring-6% to 20% of liver; light scarring-1% to 5% of liver.

What is claimed is:

1. A compound having the formula:

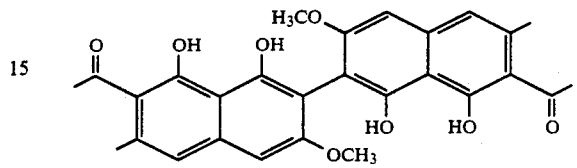

in substantially pure form.

2. A method for treating animals infected or infested with helminths, acarids, or insects, which comprises treating the animal with an effective amount of the compound of claim 1.

3. The method according to claim 2 which comprises treating the animal with about 0.1 mg compound/kilogram body weight to about 100 mg compound/kilogram body weight.

4. A composition suitable for treating helminth, acarine, or insect infections or infestations which comprises an effective amount of the compound of claim 1.

* * * * *